(12) United States Patent
Tsukada

(10) Patent No.: US 12,368,965 B2
(45) Date of Patent: Jul. 22, 2025

(54) IMAGING SYSTEM, IMAGING METHOD, AND COMPUTER PROGRAM

(71) Applicant: NEC Corporation, Tokyo (JP)

(72) Inventor: Masato Tsukada, Tokyo (JP)

(73) Assignee: NEC CORPORATION, Tokyo (JP)

( * ) Notice: Subject to any disclaimer, the term of this patent is extended or adjusted under 35 U.S.C. 154(b) by 286 days.

(21) Appl. No.: 18/015,259

(22) PCT Filed: Jul. 16, 2020

(86) PCT No.: PCT/JP2020/027722
§ 371 (c)(1),
(2) Date: Jan. 9, 2023

(87) PCT Pub. No.: WO2022/014020
PCT Pub. Date: Jan. 20, 2022

(65) Prior Publication Data
US 2023/0269490 A1    Aug. 24, 2023

(51) Int. Cl.
*H04N 23/76* (2023.01)
*H04N 5/262* (2006.01)
(Continued)

(52) U.S. Cl.
CPC .............. *H04N 23/76* (2023.01); *H04N 5/262* (2013.01); *H04N 23/63* (2023.01); *H04N 23/71* (2023.01);
(Continued)

(58) Field of Classification Search
CPC ........ H04N 23/76; H04N 5/262; H04N 23/63; H04N 23/71; H04N 23/72; H04N 23/74;
(Continued)

(56) References Cited

U.S. PATENT DOCUMENTS

2005/0280717 A1* 12/2005 Sugimoto .......... H04N 1/32128
                                                          348/222.1
2008/0267600 A1    10/2008 Omi
(Continued)

FOREIGN PATENT DOCUMENTS

JP    H10-005195 A    1/1998
JP    2001-167284 A    6/2001
(Continued)

OTHER PUBLICATIONS

International Search Report for PCT Application No. PCT/JP2020/027722, mailed on Oct. 13, 2020.
(Continued)

*Primary Examiner* — Sinh Tran
*Assistant Examiner* — Zhenzhen Wu

(57) ABSTRACT

An imaging system includes: an imaging unit that captures an image of an eye area of a target person by using an image sensor that allows imaging without saturating observed light; an acquisition unit that obtains, from the image, a first information about a first area that does not include reflection of light by an eyeglass lens of the target person, and a second information about a second area that includes the reflection of the light; and a correction unit that corrects the second information so as to reduce an influence of the reflection, on the basis of the first information. According to such an imaging system, it is possible to properly capture the iris image even when the target person is wearing eyeglasses.

11 Claims, 20 Drawing Sheets

(51) Int. Cl.
  *H04N 23/63* (2023.01)
  *H04N 23/71* (2023.01)
  *H04N 23/72* (2023.01)
  *H04N 23/74* (2023.01)
  *H04N 23/81* (2023.01)
(52) U.S. Cl.
  CPC ............. *H04N 23/72* (2023.01); *H04N 23/74* (2023.01); *H04N 23/81* (2023.01)
(58) Field of Classification Search
  CPC .... H04N 23/81; H04N 23/611; G06V 10/141; G06V 10/143; G06V 40/19; G06V 40/193; A61B 5/1171; G06T 1/00
  See application file for complete search history.

(56) References Cited

U.S. PATENT DOCUMENTS

| | | | |
|---|---|---|---|
| 2015/0085250 A1* | 3/2015 | Larsen | A61B 3/113 351/206 |
| 2015/0161472 A1 | 6/2015 | Yoshioka et al. | |
| 2016/0103484 A1* | 4/2016 | Guo | A61B 3/113 345/156 |
| 2020/0029808 A1* | 1/2020 | MacDougall | G06V 40/193 |
| 2020/0311892 A1* | 10/2020 | Pasula | G06V 10/141 |

FOREIGN PATENT DOCUMENTS

| | | |
|---|---|---|
| JP | 2003-263629 A | 9/2003 |
| JP | 2008-276328 A | 11/2008 |
| JP | 2011-165031 A | 8/2011 |
| JP | 2015-112151 A | 6/2015 |

OTHER PUBLICATIONS

M. Murata et al., "A High Near-Infrared Sensitivity Over 70-dB SNR CMOS Image Sensor With Lateral Overflow Integration Trench Capacitor," IEEE Transactions on Electron Devices, pp. 1-7, 2020.

* cited by examiner

HIDE REGISTERED IMAGE

SWITCH BETWEEN
CORRECTION AND
NO CORRECTION

HIGHLIGHTING ON
FOR REGISTERED IMAGE
AND IRIS IMAGE

IMAGING SYSTEM, IMAGING METHOD, AND COMPUTER PROGRAM

This application is a National Stage Entry of PCT/JP2020/027722 filed on Jul. 16, 2020, the contents of all of which are incorporated herein by reference, in their entirety.

TECHNICAL FIELD

This disclosure relates to an image imaging system, an imaging method, and a computer program that image an eye area of a target person.

BACKGROUND ART

A known system of this type applies light around an eye of a target person to capture an iris image. For example, Patent Literature 1 discloses a technique/technology of photographing by applying light to an eyeball at an incident angle, and of sequentially applying the light at different incident angles when a captured image is not good. Furthermore, a technique/technology that takes into account the reflection of light by eyeglasses or spectacles or the like when the iris image is captured, has also been proposed (e.g., see Patent Literatures 2 to 4).

CITATION LIST

Patent Literature

Patent Literature 1: JPH10-005195A
Patent Literature 2: JP2001-167284A
Patent Literature 3: JP2008-276328A
Patent Literature 4: JP2015-112151A

SUMMARY

Technical Problem

When the target person is wearing eyeglasses, an eyeglass lens may reflect illumination light, which may lead to fail to obtain iris features in a reflective area. Each cited document mentioned above has insufficient discussion on such problems, and there is room for improvement.

It is an example object to provide an imaging system, an imaging method, and a computer program that are configured to solve the problems described above.

Solution to Problem

An imaging system according to an example aspect of this disclosure includes: an imaging unit that captures an image of an eye area of a target person by using an image sensor that allows imaging without saturating observed light; an acquisition unit that obtains, from the image, a first information about a first area that does not include reflection of light by an eyeglass lens of the target person, and a second information about a second area that includes the reflection of the light; and a correction unit that corrects the second information so as to reduce an influence of the reflection, on the basis of the first information.

An imaging method according to an example aspect of this disclosure includes: capturing an image of an eye area of a target person by using an image sensor that allows imaging without saturating observed light; obtaining, from the image, a first information about a first area that does not include reflection of light by an eyeglass lens of the target person, and a second information about a second area that includes the reflection of the light; and correcting the second information so as to reduce an influence of the reflection, on the basis of the first information.

A computer program according to an example aspect of this disclosure operates a computer: to capture an image of an eye area of a target person by using an image sensor that allows imaging without saturating observed light; to obtain, from the image, a first information about a first area that does not include reflection of light by an eyeglass lens of the target person, and a second information about a second area that includes the reflection of the light; and to correct the second information so as to reduce an influence of the reflection, on the basis of the first information.

DESCRIPTION OF EXAMPLE EMBODIMENTS

Hereinafter, an imaging system, an imaging method, and a computer program according to example embodiments will be described with reference to the drawings.

First Example Embodiment

An imaging system according to a first example embodiment will be described with reference to FIG. 1 to FIG. 6.

Hardware Configuration

Figure 1:
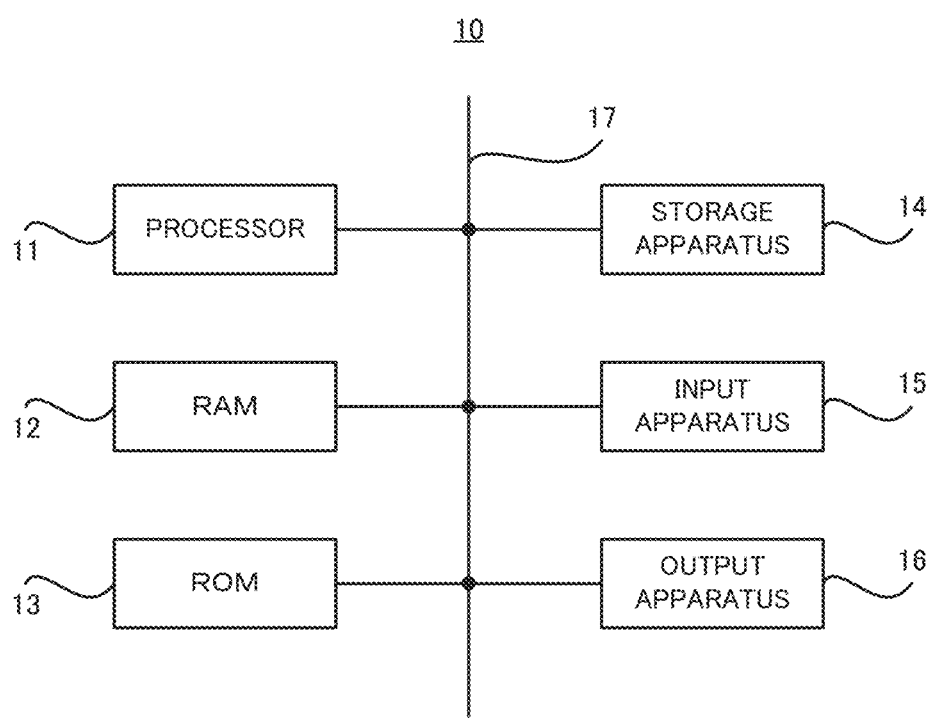
FIG. 1 is a block diagram illustrating a hardware configuration of an imaging system according to a first example embodiment.

First, with reference to FIG. 1, a hardware configuration of the imaging system according to the first example embodiment will be described. FIG. 1 is a block diagram illustrating the hardware configuration of the imaging system according to the first example embodiment.

As illustrated in FIG. 1, an imaging system 10 according to the first example embodiment includes a processor 11, a RAM (Random Access Memory) 12, a ROM (Read Only Memory) 13, and a storage apparatus 14. The imaging system 10 may also include an input apparatus 15 and an output apparatus 16. The processor 11, the RAM 12, the ROM 13, the storage apparatus 14, the input apparatus 15, and the output apparatus 16 are connected through a data bus 17.

The processor 11 reads a computer program. For example, the processor 11 is configured to read a computer program stored in at least one of the RAM 12, the ROM 13 and the storage apparatus 14. Alternatively, the processor 11 may read a computer program stored by a computer readable recording medium by using a not-illustrated recording medium reading apparatus. The processor 11 may obtain (i.e., read) a computer program from a not-illustrated apparatus that is located outside the imaging system 10 through a network interface. The processor 11 controls the RAM 12, the storage apparatus 14, the input apparatus 15, and the output apparatus 16 by executing the read computer program. Especially in the first example embodiment, when the processor 11 executes the read computer program, a functional block for processing an iris image of a target person is realized or implemented in the processor 11. As the processor 11, one of a CPU (Central Processing Unit), a GPU (Graphics Processing Unit), a FPGA (field-programmable gate array), a DSP (digital signal processor), and an ASIC (application specific integrated circuit) may be used, or a plurality of them may be used in parallel.

The RAM 12 temporarily stores the computer program to be executed by the processor 11. The RAM 12 temporarily stores the data that is temporarily used by the processor 11 when the processor 11 executes the computer program. The RAM 12 may be, for example, a D-RAM (Dynamic RAM).

The ROM 13 stores the computer program to be executed by the processor 11. The ROM 13 may otherwise store fixed data. The ROM 13 may be, for example, a P-ROM (Programmable ROM).

The storage apparatus 14 stores the data that is stored for a long term by the imaging system 10. The storage apparatus 14 may operate as a temporary storage apparatus of the processor 11. The storage apparatus 14 may include, for example, at least one of a hard disk apparatus, a magneto-optical disk apparatus, an SSD (Solid State Drive), and a disk array apparatus.

The input apparatus 15 is an apparatus that receives an input instruction from a user of the imaging system 10. The input apparatus 15 may include, for example, at least one of a keyboard, a mouse, and a touch panel.

The output apparatus 16 is an apparatus that outputs information about the imaging system 10 to the outside. For example, the output apparatus 16 may be a display apparatus (e.g., a display) that is configured to display the information about the imaging system 10.

Functional Configuration

Figure 2:
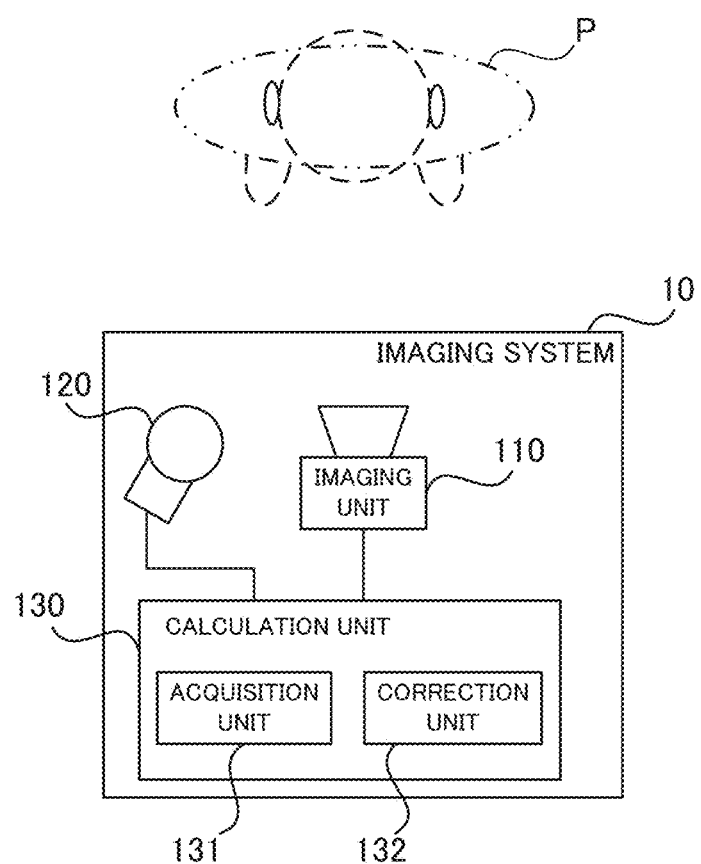
FIG. 2 is a block diagram illustrating a functional configuration of the imaging system according to the first example embodiment.

Next, with reference to FIG. 2, a functional configuration of the imaging system 10 according to the first example embodiment will be described. FIG. 2 is a block diagram illustrating the functional configuration of the imaging system according to the first example embodiment.

As illustrated in FIG. 2, the imaging system 10 according to the first example embodiment is configured to capture an image of a target person P (especially, an image of the periphery of an eye including an iris). The imaging system 10 may be configured, for example, as a part of a system that performs iris authentication of the target person P. The imaging system 10 includes an imaging unit 110, an irradiation unit 120, and a calculation unit 130.

The imaging unit 110 is configured, for example, as a camera disposed at a position at which the target person P can be captured. The imaging unit 110 has resolution that allows features of the iris (hereinafter referred to "iris features" as appropriate) of the target person P. The imaging unit 110 includes an image sensor having a dynamic range that allows imaging without saturating reflected light from the vicinity of an eye area. More specifically, the imaging unit 110 includes an image sensor having a dynamic range in which a pixel value is not saturated in both an area that does not include reflection of light (hereinafter referred to as a "first area" as appropriate) even when light reflection occurs on a lens surface of eyeglasses that the target person P is wearing, and an area that includes the reflection of light (hereinafter referred to as a "second area" as appropriate). As an example of such an image sensor, an image sensor illustrated in Non-Patent Literature 1 can be used.

Non-Patent Literature 1: M. Murata et al., "A High Near-Infrared Sensitivity Over 70-dB SNR CMOS Image Sensor With Lateral Overflow Integration Trench Capacitor," IEEE TRANSACTIONS ON ELECTRON DEVICES, pp. 1-7, 2020.

When imaging is performed by the imaging unit 110, exposure, shutter speed, gain, and the like are adjusted as appropriate such that the iris features of the target person P are effectively captured as an image. The image of the eye area of the target person P captured by the imaging unit 110 is configured to be outputted to the calculation unit 130.

The irradiation unit 120 applies illumination light to the target person P when the imaging unit 110 captures the image of the target person P. The irradiation timing of the irradiation unit 120 may be synchronized with the imaging timing of the imaging unit 110. The number of the irradiation unit 120 is not limited to one, and a plurality of irradiation units 120 may be provided. In this case, the illumination light may be applied by the plurality of irradiation units 120 simultaneously, or the illumination light may be applied from a part of the irradiation units 120 depending on the situation. When the plurality of irradiation units 120 are provided, they may be arranged two-dimensionally (i.e., on the same plane) or may be arranged three-dimensionally.

The calculation unit 130 is configured to perform various processes on the image captured by the imaging unit 110. The calculation unit 130 may be configured, for example, as a part of the processor 11 in FIG. 1. The calculation unit 130 includes an acquisition unit 131 and a correction unit 132 as processing blocks for realizing the function.

The acquisition unit 131 is configured to obtain information about the iris from the image captured by the imaging unit 110. The acquisition unit 131 is especially configured to obtain a first information about the first area (i.e., the area that does not include the reflection of light by an eyeglass lens) and a second information about the second area (i.e., the area that includes the reflection of light by the eyeglass lens). The first information and the second information are obtained, for example, as the pixel value. When the light reflection does not occur on the eyeglass lens, the acquisition unit 131 may be configured to obtain only the first information. The first information and the second information obtained by the acquisition unit 131 are configured to be outputted to the correction unit 132.

The correction unit 132 is configured to correct the second information on the basis of the first information. More specifically, the correction unit 132 corrects the second information such that an influence of the light reflection on the eyeglass lens included in the second information is reduced (preferably to be zero).

Modified Example

Figure 3:
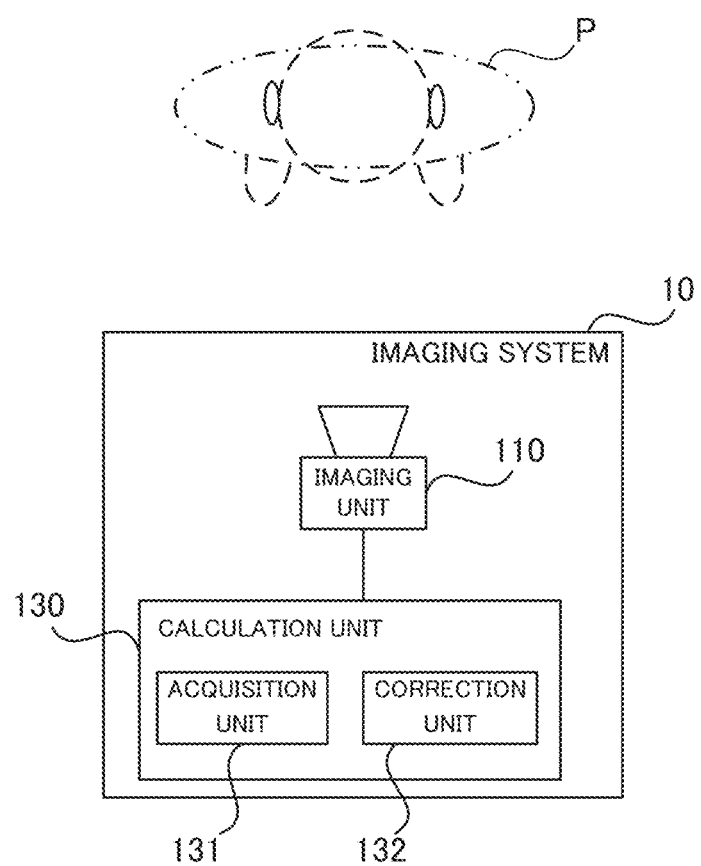
FIG. 3 is a block diagram illustrating a functional configuration of an imaging system according to a modified example of the first example embodiment.

Next, with reference to FIG. 3, the imaging system 10 according to a modified example of the first example embodiment will be described. FIG. 3 is a block diagram illustrating a functional configuration of the imaging system according to the modified example of the first example embodiment. In FIG. 3, the same components as those illustrated in FIG. 2 carry the same reference numerals.

As illustrated in FIG. 3, the imaging system 10 according to the modified example includes the imaging unit 110 and the calculation unit 130. That is, the imaging system 10 may not necessarily include the irradiation unit 120. In this case, the target person P may be illuminated with light from outside lighting of the system (e.g., fluorescent lamps, etc.), or with natural light or the like.

Influence of Light Reflection by Eyeglass lens

Figure 4:
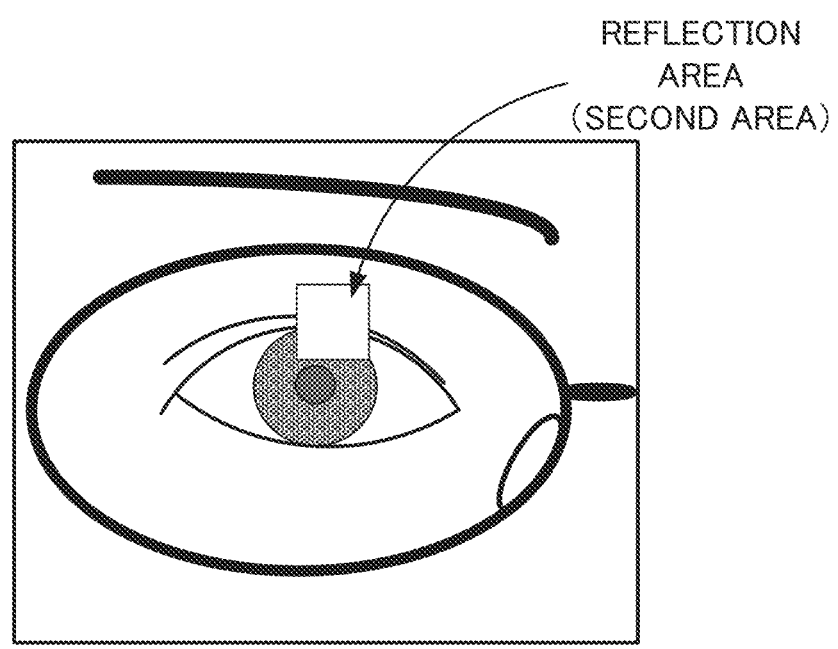
FIG. 4 is a diagram illustrating an imaging example when light reflection occurs on an eyeglass lens.

Next, the influence of the light reflection that occurs on the eyeglass lens on the image will be described with reference to FIG. 4. FIG. 4 is a diagram illustrating an imaging example when the light reflection occurs on the eyeglass lens.

As illustrated in FIG. 4, when the target person P is wearing eyeglasses, the illumination light applied from the irradiation unit 120 may be reflected by the eyeglass lens, which may influence the image captured by the imaging unit 110. Specifically, the second area, which is influenced by the light reflection, may overlap an area of the iris of the target person P, and this may make it hardly possible to properly obtain the iris features. In particular, when the dynamic range of the image sensor is narrow (e.g., about 50 dB), the pixel value of the second area influenced by the reflection on the eyeglass lens may be saturated, and the iris features may not be obtained at all. To avoid such a situation, the imaging system 10 according to the first example embodiment includes the image sensor having the dynamic range that allows the imaging without saturating reflected light, as already described.

Path of Reflected Light

Figure 5:
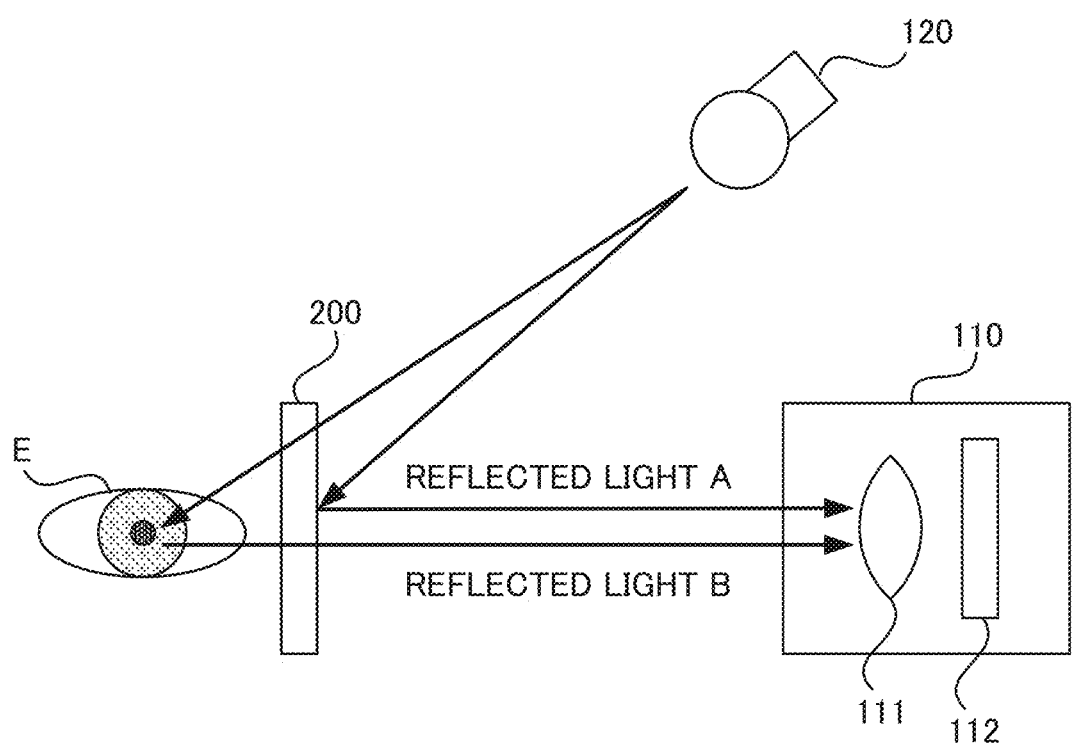
FIG. 5 is a conceptual diagram illustrating a path of light reflected by an iris of a target person and a path of light reflected by the eyeglass lens.

Next, a path of the illumination light, which is applied from the irradiation unit 120, up to the imaging unit 110 will be specifically described with reference to FIG. 5. FIG. 5 is a conceptual diagram illustrating the path of the light reflected by the iris of the target person and the light reflected by the eyeglass lens.

As illustrated in FIG. 5, the illumination light applied from the irradiation unit 120 is divided into a component of reflected light A reflected by a front or rear surface of an eyeglass lens 200 toward the imaging unit 110 and a component of reflected light B reflected by an iris E of the target person P toward the imaging unit 110. Here, reflected light from the first area includes the reflected light B. On the other hand, reflected light from the second area includes both the reflected light A and the reflected light B. Therefore, if a correction of separating those derived from the component of the reflected light A can be performed on the second information about the second area, it is possible to reduce the influence of the reflection on the eyeglass lens 200.

Flow of Operation

Figure 6:
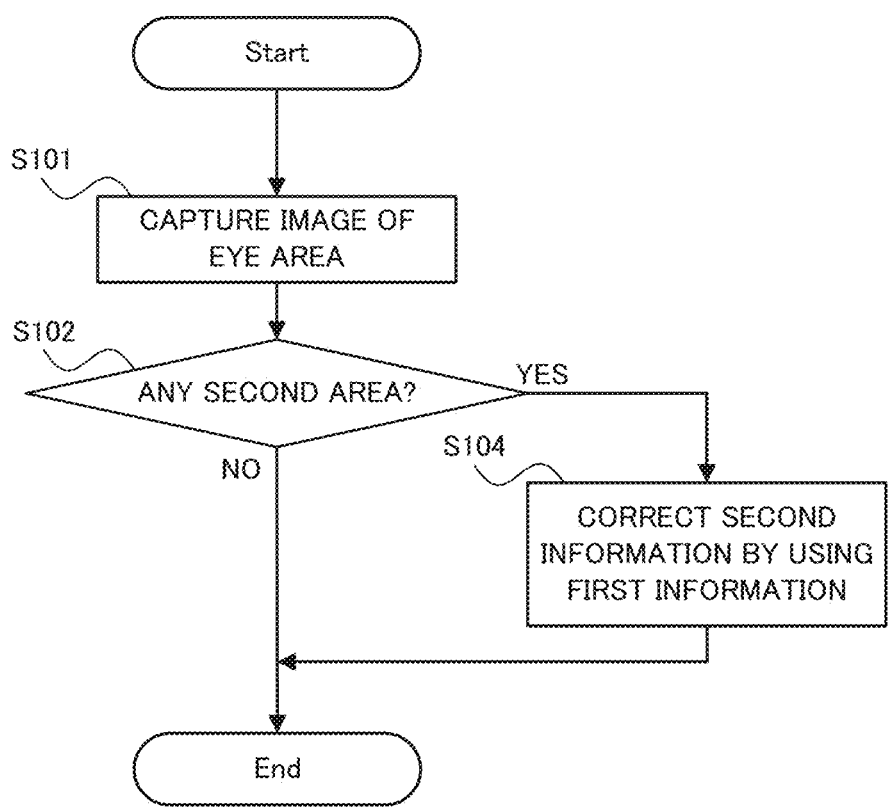
FIG. 6 is a flowchart illustrating a flow of operation of the imaging system according to the first example embodiment.

Next, with reference to FIG. 6, a flow of operation of the imaging system 10 according to the first example embodiment will be described. FIG. 6 is a flowchart illustrating the flow of the operation of the imaging system according to the first example embodiment.

As illustrated in FIG. 6, in operation of the imaging system 10 according to the first example embodiment, first, the imaging unit 110 captures the image of the eye area of the target person P (step S101).

Subsequently, the acquisition unit 131 obtains the first information and the second information, and determines whether or not there is any second area (step S102). In other words, the acquisition unit 131 determines whether or not there is an area that includes the reflection of light by the eyeglass lens 200. Whether or not there is any second area can be determined, for example, by whether or not there is a part where amount of light is locally increased.

When there is no second area (the step S102: NO), there is only the first area, and there is no need to consider the influence of light reflection. Therefore, in this case, a series of processing steps is ended.

On the other hand, when there is the second area (the step S102: YES), it is hard to obtain the iris features in the second area as it is. Therefore, in this case, the correction unit 132 corrects the second information on the basis of the first information (step S104). A specific correction method here will be described in detail in a fourth example embodiment later.

Technical Effect

Next, a technical effect obtained by the imaging system 10 according to the first example embodiment will be described.

As described in FIG. 1 to FIG. 6, in the imaging system 10 according to the first example embodiment, the second information that indicates the reflection of light by the eyeglass lens 200 is corrected by the correction unit 132. Consequently, it is possible to reduce the influence of the reflection on the eyeglass lens 200, and it is also possible to obtain the iris features of the target person P for the second area.

Second Example Embodiment

The imaging system 10 according to a second example embodiment will be described with reference to FIG. 7 and FIG. 8. The second example embodiment is partially different from the first example embodiment described above only in configuration and operation, and may be the same as the first example embodiment, for example, in hardware configuration (see FIG. 1). Therefore, in the following, a description of the parts that overlap the first example embodiment will be omitted as appropriate.

Figure 7:
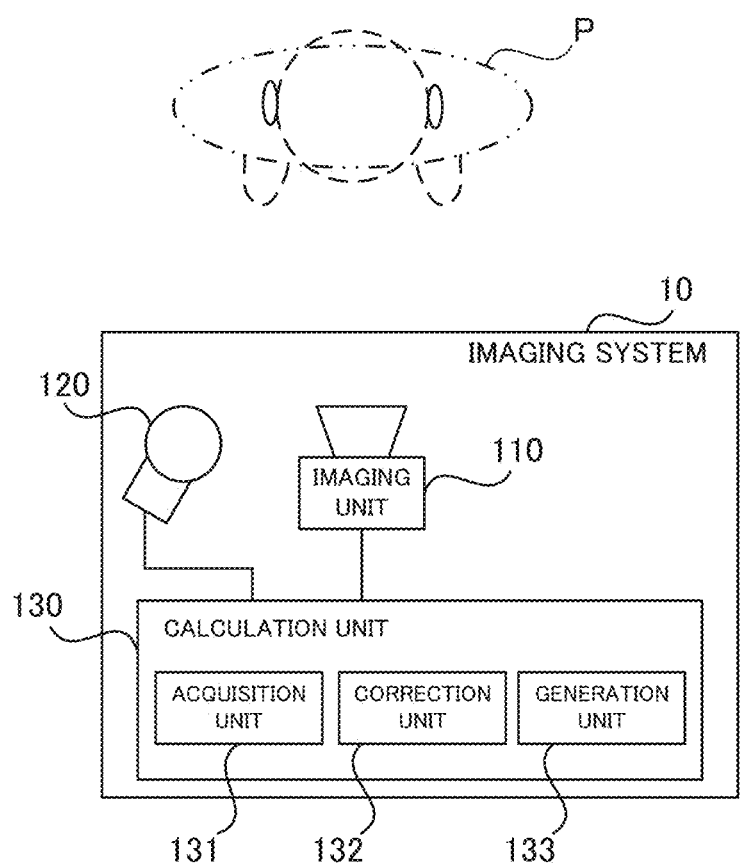
FIG. 7 is a block diagram illustrating a functional configuration of an imaging system according to a second example embodiment.

As illustrated in FIG. 7, the imaging system 10 according to the second example embodiment includes the imaging unit 110, the irradiation unit 120, and the calculation unit 130. In particular, the calculation unit 130 according to the second example embodiment includes the acquisition unit 131, the correction unit 132, and a generation unit 133. That is, the calculation unit 130 according to the second example embodiment further includes the generation unit 133 in addition to the configuration in the first example embodiment.

The generation unit 133 is configured to generate the iris image including the iris features of the target person P from the first information obtained by acquisition unit 131 and from the second information corrected by the correction unit 132. For example, the generation unit 133 generates the iris image of the target person P by using an iris information included in the first information (i.e., the iris information obtained originally without being influenced by the light reflection) and an iris information included in the corrected second information (i.e., the iris information obtained because the influence of the light reflection is reduced by the correction). The generation unit 133 may have a function of outputting the generated iris image.

Flow of Operation

Next, with reference to FIG. 8, a flow of operation of the imaging system 10 according to the first example embodiment will be described. FIG. 8 is a flowchart illustrating the flow of the operation of the imaging system according to the second example embodiment. In FIG. 8, the same steps as those illustrated in FIG. 6 carry the same reference numerals.

Figure 8:
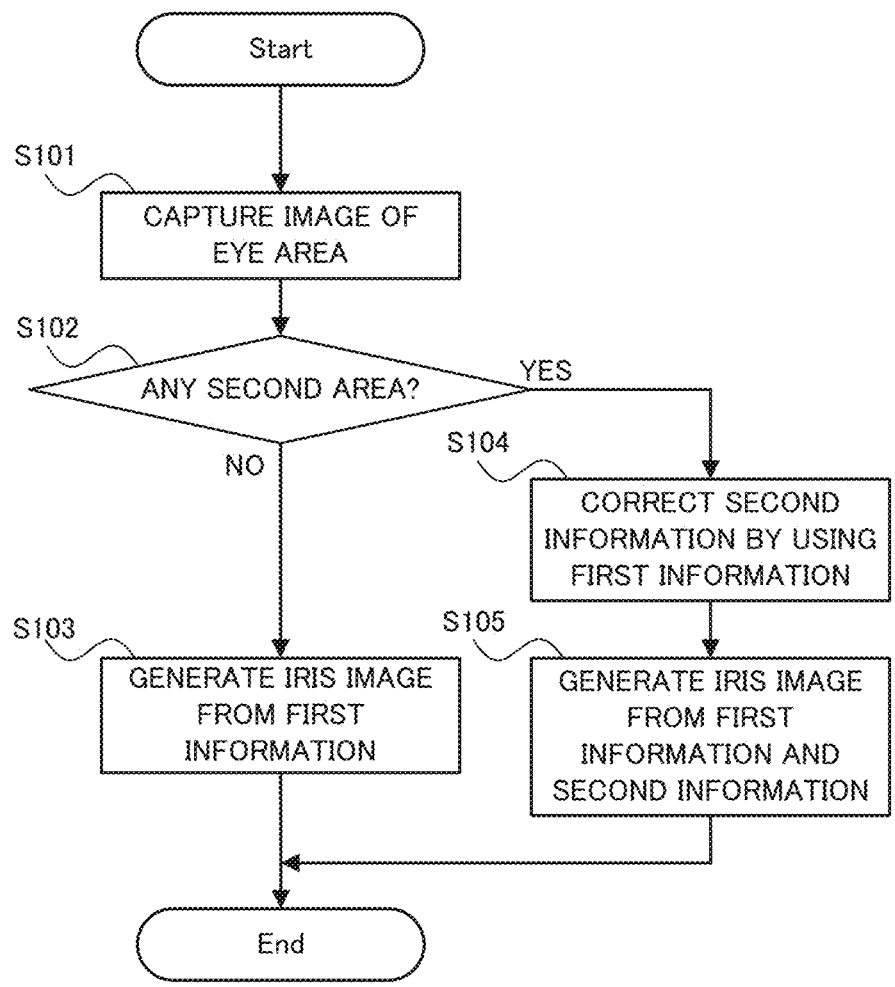
FIG. 8 is a flowchart illustrating a flow of operation of the imaging system according to the second example embodiment.

As illustrated in FIG. 8, in operation of the imaging system 10 according to the second example embodiment, first, the imaging unit 110 captures the image of the eye area of the target person P (the step S101). Subsequently, the acquisition unit 131 obtains the first information and the second information, and determines whether or not there is any second area (the step S102).

When there is no second area (the step S102: NO), there is only the first area, and there is no need to consider the influence of light reflection. Therefore, in this case, the generation unit 133 generates the iris image from the first information about the first area (step S103).

On the other hand, when there is the second area (the step S102: YES), it is hard to obtain the iris features in the second area as it is. Therefore, in this case, the correction unit 132 corrects the second information on the basis of the first information (the step S104). Then, the generation unit 133 generates the iris image from the first information and the corrected second information (step S105).

Technical Effect

Next, a technical effect obtained by the imaging system 10 according to the second example embodiment will be described.

As described in FIG. 7 and FIG. 8, in the imaging system 10 according to the second example embodiment, the iris image is generated from the first information and the corrected second information. Thus, even when the light reflection by the eyeglass lens 200 occurs, it is possible to properly generate the iris image. Such a technical effect is significantly demonstrated, for example, when iris authentication that requires precise iris features is performed. For example, this eliminates a need for the target person P to remove eyeglasses, or reduces a risk of re-imaging, which greatly improves convenience when the iris image is captured.

Third Example Embodiment

The imaging system 10 according to a third example embodiment will be described with reference to FIG. 9. The third example embodiment is partially different from the first and second example embodiments described above only in operation, and may be the same as the first and second example embodiments in configuration (see FIG. 1, FIG. 2, FIG. 3, and FIG. 7). Therefore, in the following, a description of the parts that overlap the first and second example embodiments will be omitted as appropriate.

Flow of Operation

First, with reference to FIG. 9, a flow of operation of the imaging system 10 according to the third example embodiment will be described. FIG. 9 is a flowchart illustrating the flow of the operation of the imaging system according to the third example embodiment. In FIG. 9, the same steps as those illustrated in FIG. 6 and FIG. 8 carry the same reference numerals.

Figure 9:
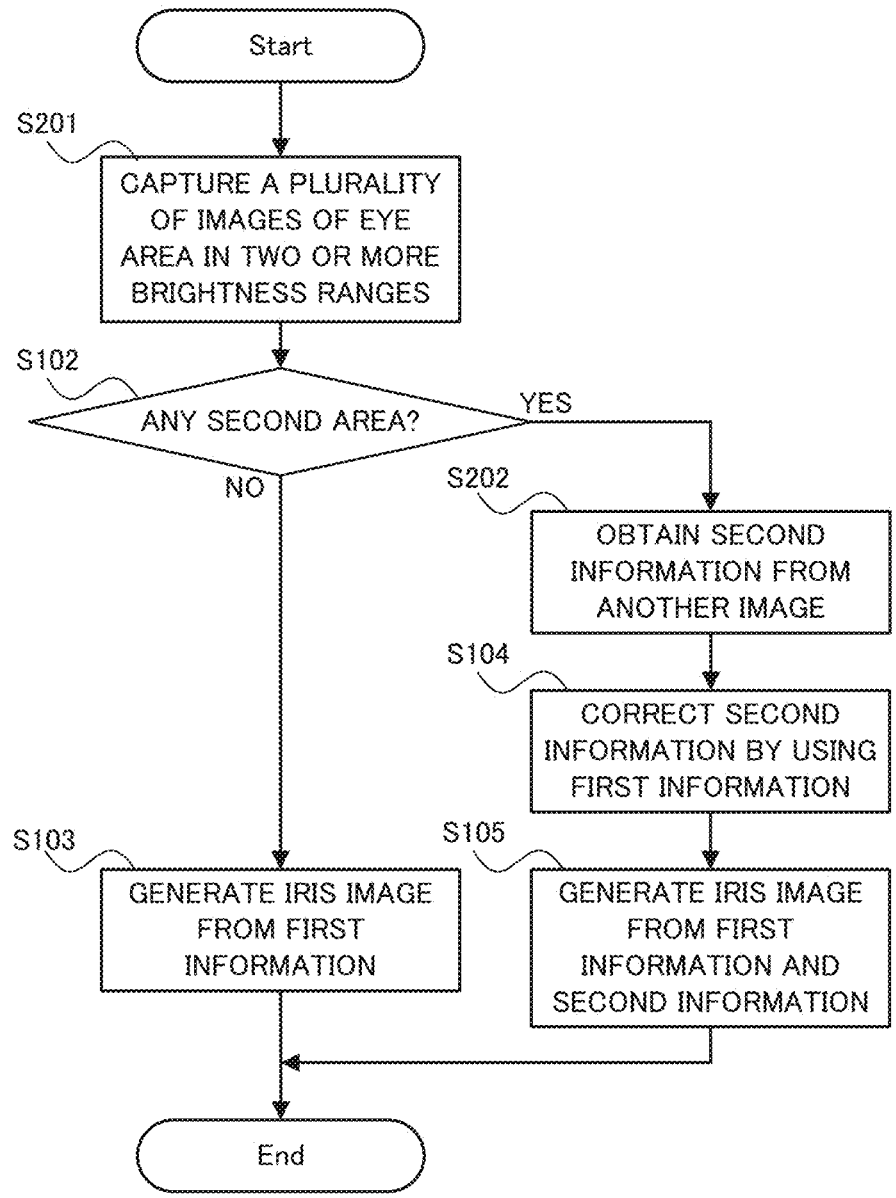
FIG. 9 is a flowchart illustrating a flow of operation of an imaging system according to a third example embodiment.

As illustrated in FIG. 9, in operation of the imaging system 10 according to the third example embodiment, first, the imaging unit 110 captures a plurality of images of the eye area of the target person P in two or more different brightness ranges (step S201). For example, when images are captured in two brightness ranges, the imaging unit 110 may capture one image in a relatively low brightness range and may capture one image in a relatively high brightness range.

Subsequently, the acquisition unit 131 obtains the first information and the second information from one image, and determines whether or not there is any second area (the step S102). The one image is preferably an image captured in a brightness range from which the iris features can be properly obtained from the first information (e.g., an image with the lowest brightness range).

When there is no second area (the step S102: NO), there is only the first area, and thus, the generation unit 133 generates the iris image from the first information obtained from the one image (the step S103).

On the other hand, when there is the second area (the step S102: YES), the acquisition unit 131 obtains the second information from another image (i.e., an image with a brightness range that is different from that of the one image) (step S202). This another image is preferably an image that allows the iris features of the second area to be obtained to some extent (e.g., an image with a brightness range that is higher than that of the one image).

Then, the correction unit 132 corrects the second information on the basis of the first information (the step S104). Then, the generation unit 133 generates the iris image from the first information and the corrected second information (the step S105).

Technical Effect

Next, a technical effect obtained by the imaging system 10 according to the third example embodiment will be described.

As described in FIG. 9, in the imaging system 10 according to the third example embodiment, the iris image of the target person P is generated by using a plurality of images captured in two or more brightness ranges. Here, if the brightness range is fixed, the iris features of both the first area and the second area may not be obtained from the image captured in the fixed brightness range. In the third example embodiment, however, since a plurality of images captured in two or more brightness ranges are used, it is possible to separately obtain the first information and second information from the respective images. Thus, it is possible to generate the iris image of the target person P, more properly.

Modified Example

Figure 10:
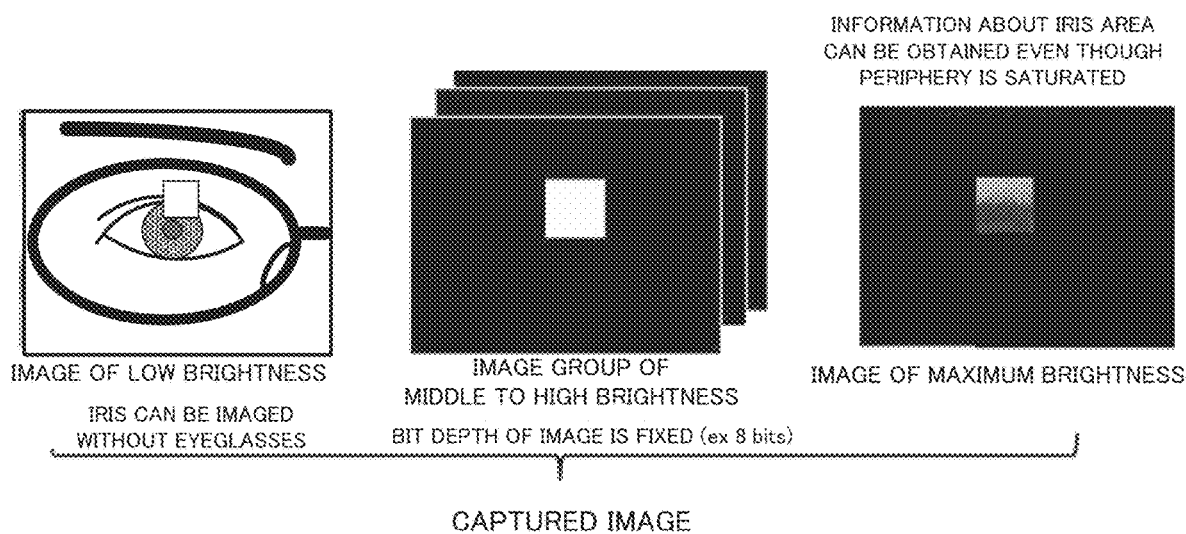
FIG. 10 is a diagram illustrating an example of a plurality of images captured in different brightness ranges.

Here, with reference to FIG. 10, the imaging system 10 according to a modified example of the third example embodiment will be described. FIG. 10 is a diagram illustrating an example of a plurality of images captured in different brightness ranges.

As illustrated in FIG. 10, in the imaging system 10 according to the modified example, the imaging unit 110 captures the images of the target person P in five different brightness ranges. In this example, the iris features about the first area can be obtained from an image of low brightness with the lowest brightness range, while the iris features about the second area cannot be obtained. Specifically, in the image of low brightness, the pixel value of the second area is saturated (when each image has a bit depth of 8 bits, the saturated pixel value is 255).

In such a case, the acquisition unit 131 obtains the second information about the second area from a non-saturated image in which the pixel value of the second area is not saturated. Specifically, the second information is obtained from an image of maximum brightness with the highest brightness range. In the image of maximum brightness, as can be seen from FIG. 10, the pixel value is saturated in a peripheral part other than the second area, but the pixel value is not saturated in the second area, and the iris features can be obtained as the second information.

Thus, even when the pixel value of the second area is saturated in the image of low brightness, it is possible to properly generate the iris image by obtaining the second information from the image in which the pixel value is not saturated in the second area. The above-described example describes that the second information is obtained from the image of maximum brightness; however, when the pixel value of the second area is not saturated even in an image group of middle to high brightness, the second information may be obtained therefrom.

Fourth Example Embodiment

The imaging system 10 according to a fourth example embodiment will be described with reference to FIG. 11 to FIG. 14. The fourth example embodiment is an example embodiment for describing a specific method of correcting the second information in the first to third example embodiments described above (i.e., a specific operation example of the correction unit 132), and may be the same as the first example embodiment (see FIG. 1, FIG. 2 and FIG. 5), the second example embodiment (see FIG. 8), or the third example embodiment (see FIG. 9) in configuration and flow of operation. Therefore, in the following, a description of the parts that overlap those already described will be omitted as appropriate.

Amount of Light in First Area and Second Area

Figure 11:
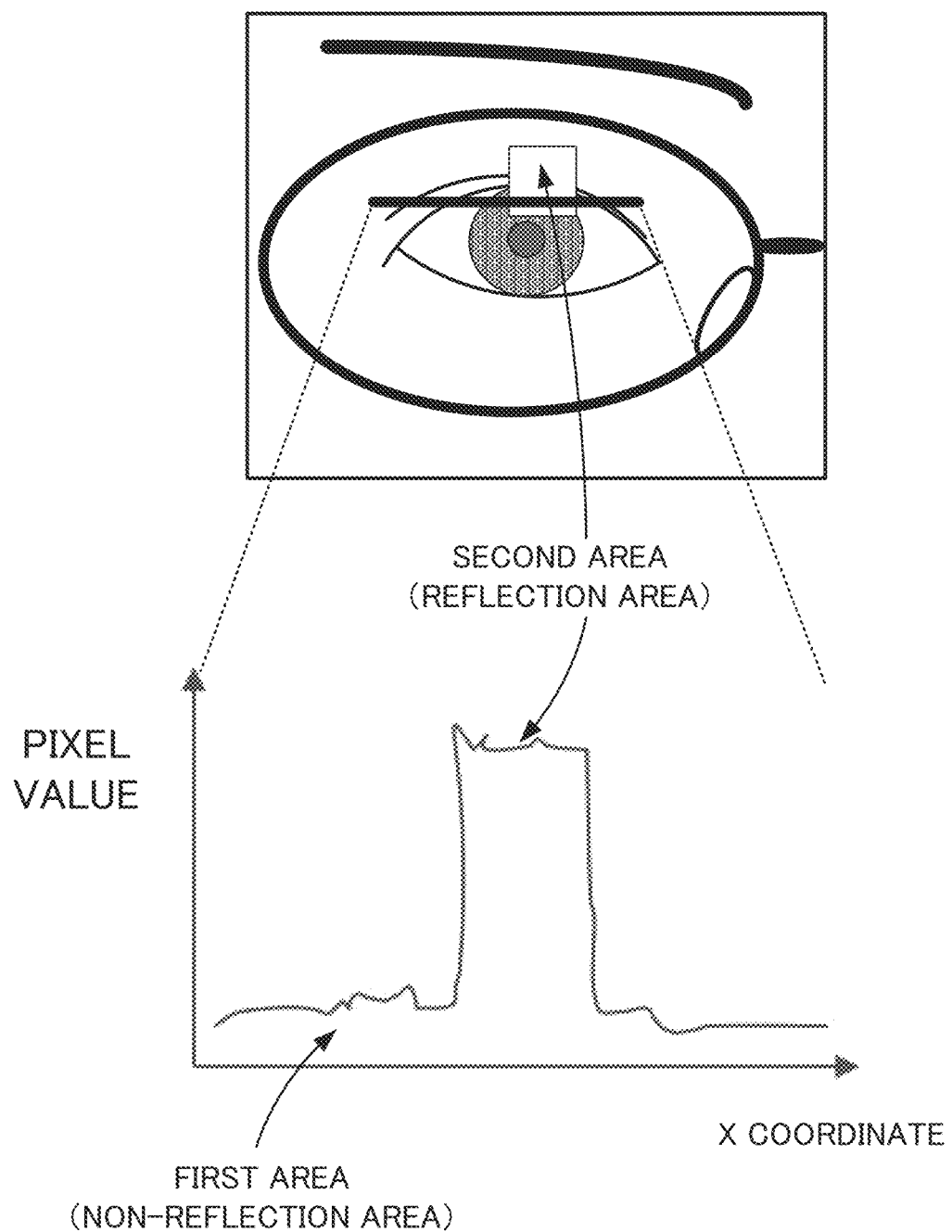
FIG. 11 is a graph illustrating an example of amount of light observed in a first area and a second area.

First, with reference to FIG. 11, the amount of light of the reflected light in the first area and second area will be described. FIG. 11 is a graph illustrating an example of the amount of light observed in the first area and the second area. This graph is a plot of values obtained by scanning a thick line part that crosses the first area and the second area in FIG. 11, in a lateral direction (i.e., an X-axis direction).

As illustrated in FIG. 11, since observed light has a relatively small amount of light in the first area in which the light reflection does not occur on the eyeglass lens 200, the pixel value is reduced. On the other hand, since the observed light has an increased amount of light in the second area in which the light reflection occurs on the eyeglass lens 200, the pixel value is increased.

Here, for the reflected light reflected by the iris (i.e., the reflected light B in FIG. 4), the amount of light varies due to visual features of the iris. On the other hand, for the reflected light reflected by the eyeglass lens 200 (i.e., the reflected light A in FIG. 4), the amount of light is substantially uniform because there are no visual features, such as a pattern, in the eyeglass lens 200. By using this difference in the features, it is possible to perform the correction of separating the component of the reflected light A and the component of the reflected light B (in other words, a correction of removing only the component of the reflected light A).

Correction of Pixel Value

Figure 12:
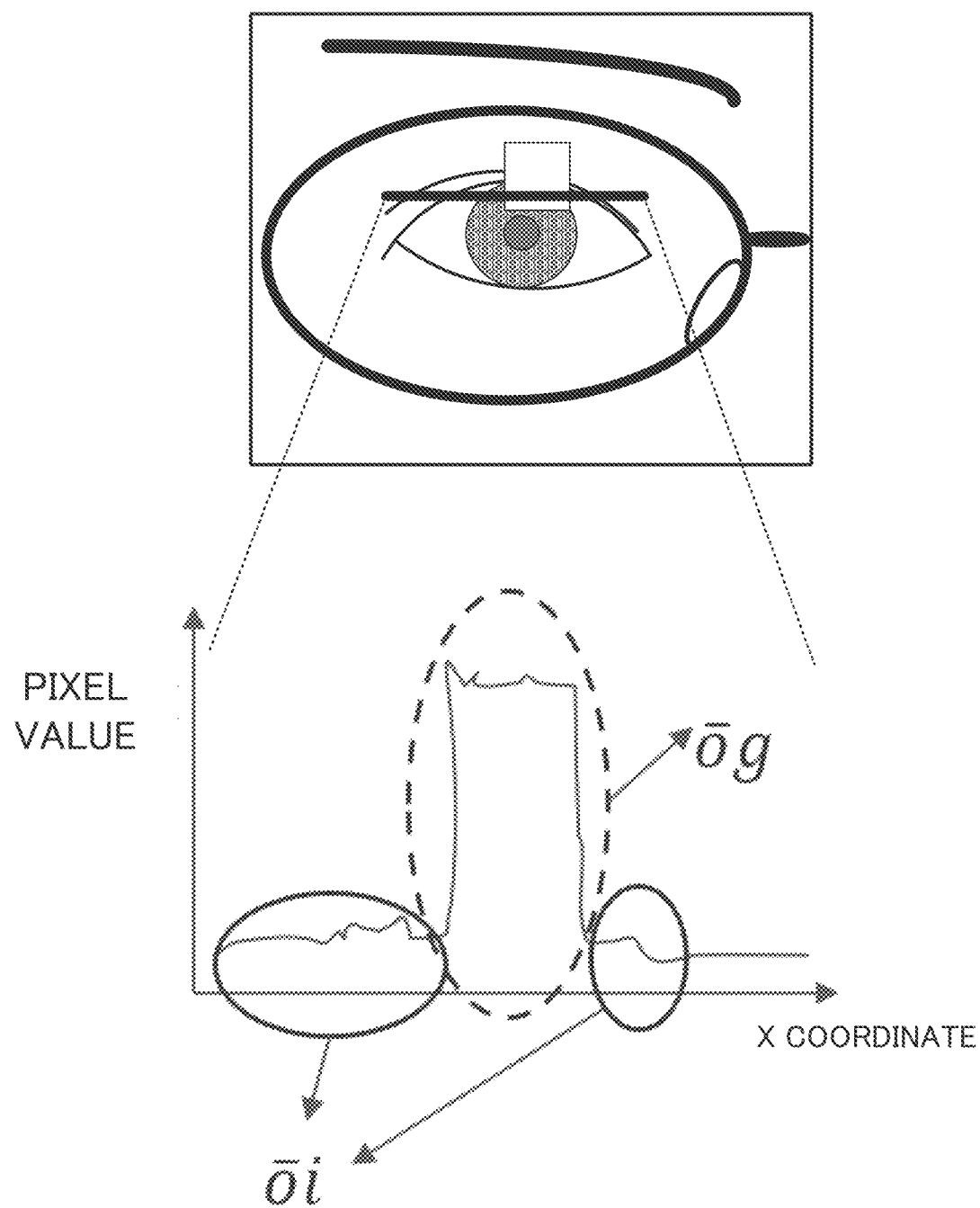
FIG. 12 is a conceptual diagram illustrating a method of calculating an average value of pixel values of the first area and an average value of pixel values of the second area.
Figure 13:
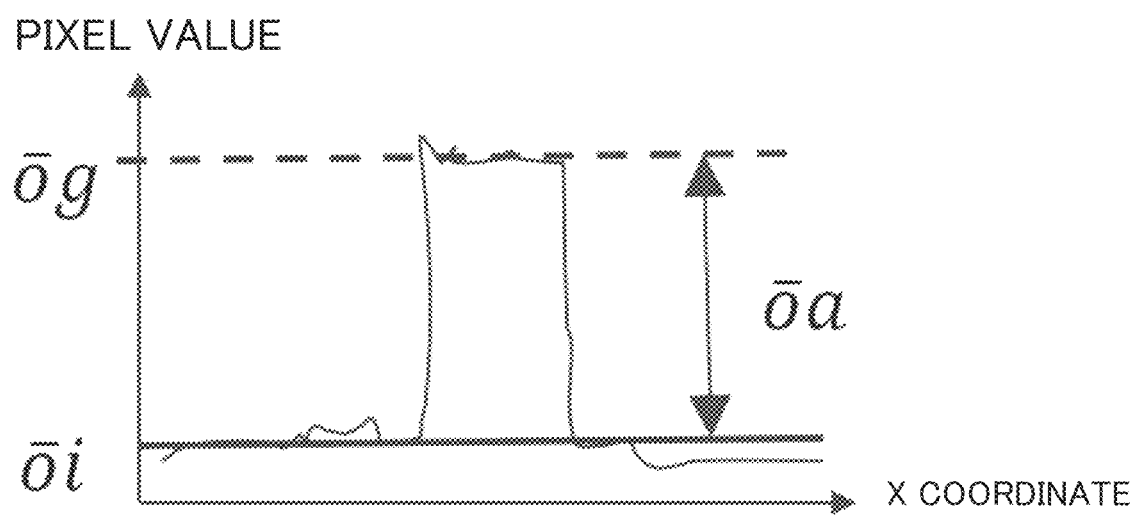
FIG. 13 is a graph illustrating a difference between the average value of the pixel values of the first area and the average value of the pixel values of the second area.
Figure 14:
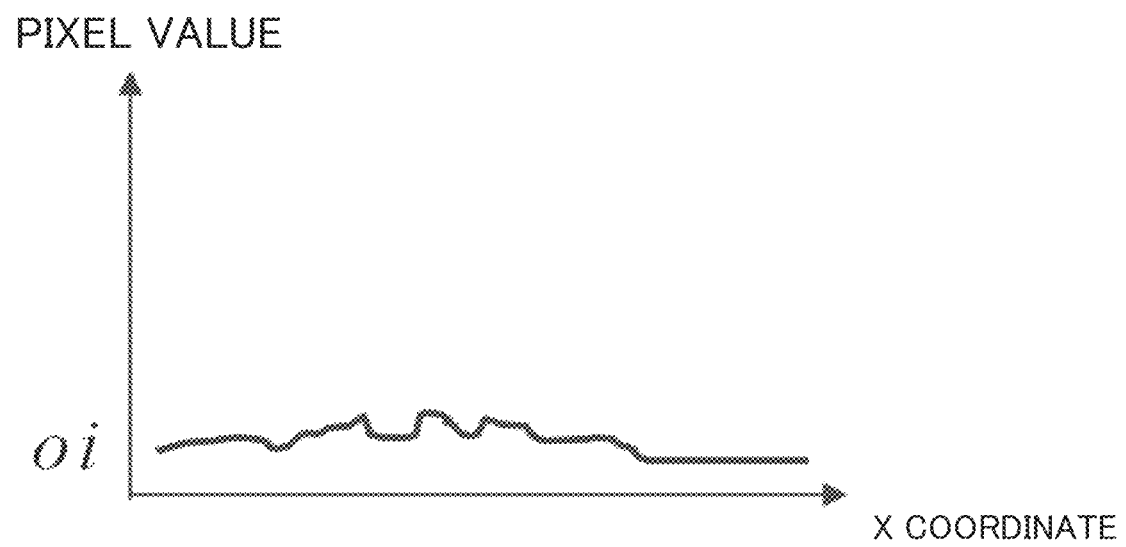
FIG. 14 is a graph illustrating an example of a pixel value after correction by using the average value of the pixel values.

Next, a method of correcting the pixel value will be described with reference to FIG. 12 to FIG. 14. FIG. 12 is a conceptual diagram illustrating a method of calculating an average value of pixel values of the first area and an average value of pixel values of the second area. FIG. 13 is a graph illustrating a difference between the average value of the pixel values of the first area and the average value of the pixel values of the second area. FIG. 14 is a graph illustrating an example of a pixel value after correction by using the average value of the pixel values.

In FIG. 12, an area surrounded by a solid line indicates the pixel value of the iris area (i.e., the pixel value of the first area). An area surrounded by a dotted line indicates the pixel value of the area influenced by the light reflection of the eyeglass lenses 200 (i.e., the pixel value of the second area). The first area and the second area can be easily distinguished by using such a characteristic that they have significantly different pixel values from each other.

In the imaging system 10 according to the fourth example embodiment, the correction unit 132 calculates an average value $\bar{O}_i$ of the pixel values of the first area, wherein $\bar{O}$ means a letter O with macron. The correction unit 132 also calculates an average value $\bar{O}_g$ of the pixel values of the second area. Here, the average value $\bar{O}_i$ indicates the average value of the light reflected by the iris (i.e., the reflected light B in FIG. 4). The average value $\overline{O}g$ indicates the average value of the sum of the light reflected by the iris and the light reflected by the eyeglass lens 200 (i.e., the sum of the reflected light A and the reflected light B in FIG. 4). Therefore, the average value $\overline{O}a$ of the reflected light A can be calculated by using the following equation (1).

[Equation 1]

$$\overline{O}a = \overline{O}g - \overline{O}i \qquad (1)$$

Furthermore, by using a coefficient α considering a predetermined margin, calculation may be performed as in the following equation (2).

[Equation 2]

$$\overline{O}a = \overline{O}g - \overline{O}i + \alpha \qquad (2)$$

Here, α may be a value that is statistically determined by experiments, or may be a value that can be arbitrarily set by a user. When the generated iris image is displayable as in a fifth example embodiment described later, the value of α may be adjusted on a display screen to update the display of the iris image at each time of the adjustment.

As illustrated in FIG. 13, the average value $\overline{O}a$ of the reflected light A reflected by the eyeglass lens 200 can be represented on a graph as a length between a straight line indicating the average value $\overline{O}i$ and a straight line indicating the average value $\overline{O}g$. When the average value $\overline{O}a$ is obtained, not only one line on the image illustrated in FIG. 12, but also a plurality of lines may be used to obtain the average value of the pixel values of each area.

The correction unit 132 calculates a pixel value Oi(x,y) of the first area from a pixel value Og(x,y) at a coordinate position (x,y) on the image of the second area (see Equation (3) below).

[Equation 3]

$$Oi(x,y) = Og(x,y) - \overline{O}a \qquad (3)$$

By following the above procedure, as illustrated in FIG. 14, the pixel value Oi(x,y) obtained by removing the influence of the reflected light on the eyeglass lens 200 from the pixel value of the second area is calculated. By obtaining the pixel value Oi(x,y) for all the pixels influenced by the reflected light from the eyeglass lens 200, it is possible to generate the iris image that captures the visual features of the eyes of the target person P.

Fifth Example Embodiment

The imaging system 10 according to a fifth example embodiment will be described with reference to FIG. 15 to FIG. 18B. The fifth example embodiment is partially different from the first to fourth example embodiments described above only in configuration, and may be the same as the first example embodiment (see FIG. 1, FIG. 2 and FIG. 5), the second example embodiment (see FIG. 7 and FIG. 8), or the third example embodiment (see FIG. 9) in hardware configuration and flow of operation or the like. Therefore, in the following, a description of the parts that overlap those already described will be omitted as appropriate.

Functional Configuration

Figure 15:
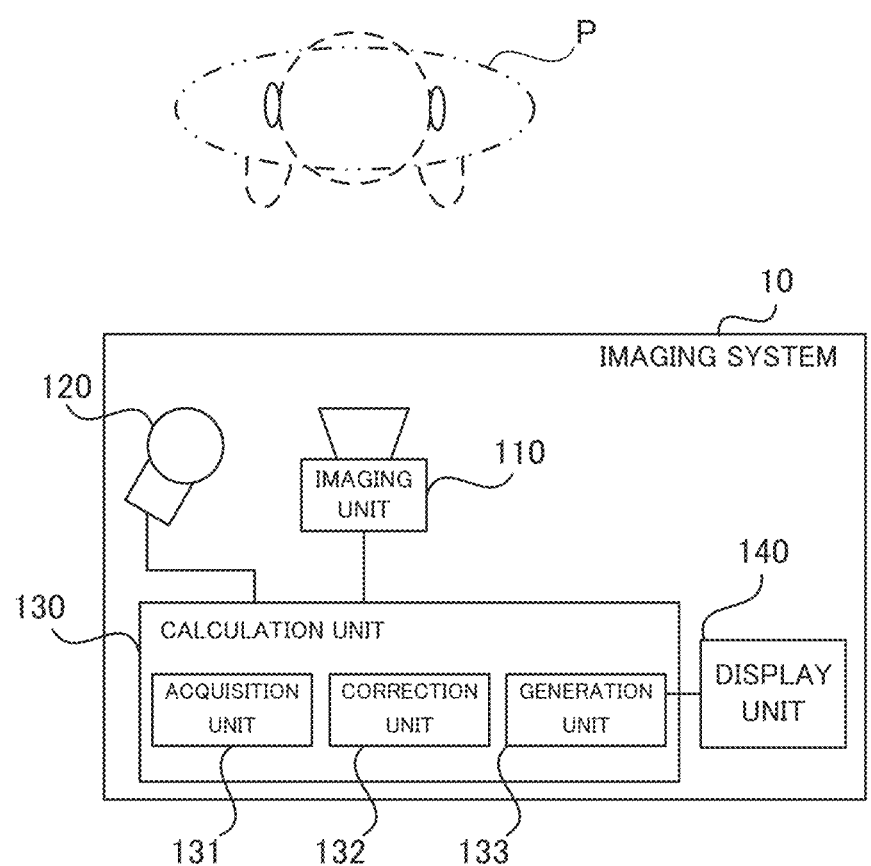
FIG. 15 is a block diagram illustrating a functional configuration of an imaging system according to a fifth example embodiment.

First, with reference to FIG. 15, a functional configuration of the imaging system 10 according to a fifth example embodiment will be described. FIG. 15 is a block diagram illustrating the functional configuration of the imaging system according to the fifth example embodiment. In FIG. 12, the same components as those illustrated in FIG. 2 carry the same reference numerals.

As illustrated in FIG. 15, the imaging system 10 according to the fifth example embodiment includes the imaging unit 110, the irradiation unit 120, the calculation unit 130, and a display unit 140. That is, the imaging system 10 according to the fifth example embodiment further includes the display unit 140 in addition to the configuration in the first example embodiment (see FIG. 2).

The display unit 140 is configured as a monitor having a display, for example. The display unit 140 may be configured as a part of the output apparatus 16 illustrated in FIG. 1. The display unit 140 is configured to display at least one of the iris image generated by the generation unit 133 and a registered image for an authentication process that uses the iris image.

Display Example

Next, a display example of the imaging system 10 according to the fifth example embodiment will be described with reference to FIG. 16A to FIG. 18B. A first display example to a third display example described below may be combined to use as appropriate.

First Display Example

Figure 16A:
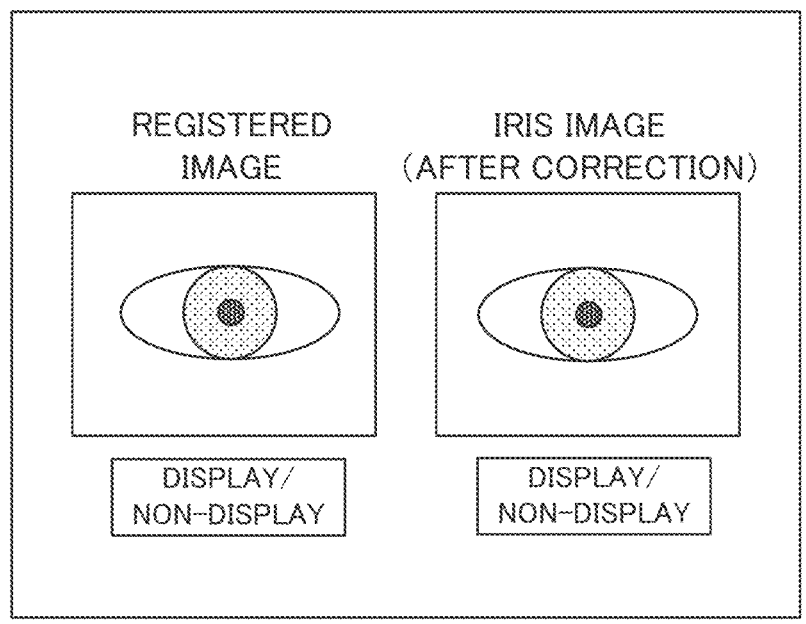
FIG. 16A and FIG. 16B are Version 1 of a diagram illustrating a display example in the imaging system according to the fifth example embodiment.
Figure 16B:
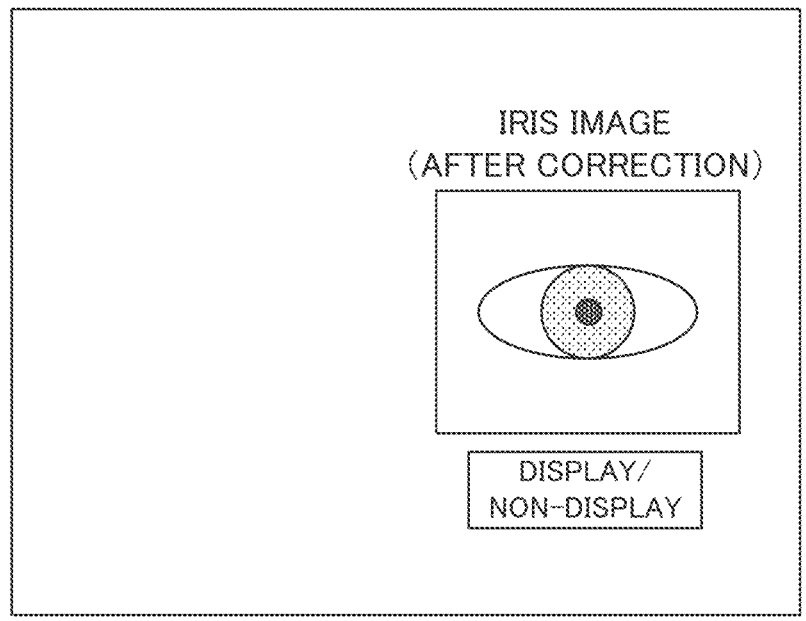

With reference to FIG. 16A and FIG. 16B, a first display example will be described. FIG. 16A and FIG. 16B are Version 1 of a diagram illustrating the display example in the imaging system according to the fifth example embodiment.

As illustrated in FIG. 16A, the display unit 140 may display the registered image and the iris image side by side. At this time, the display unit 140 may perform display in such a manner that display/non-display of the registered image and the iris image is switchable. Specifically, a button for switching between display and non-display may be displayed below each image. In this case, when a button for hiding the registered image is pressed, the registered image is hidden and only the iris image is displayed, as illustrated in FIG. 16B. When only one of the images is displayed, an image to be displayed may be enlarged and displayed in the center.

Second Display Example

Figure 17A:
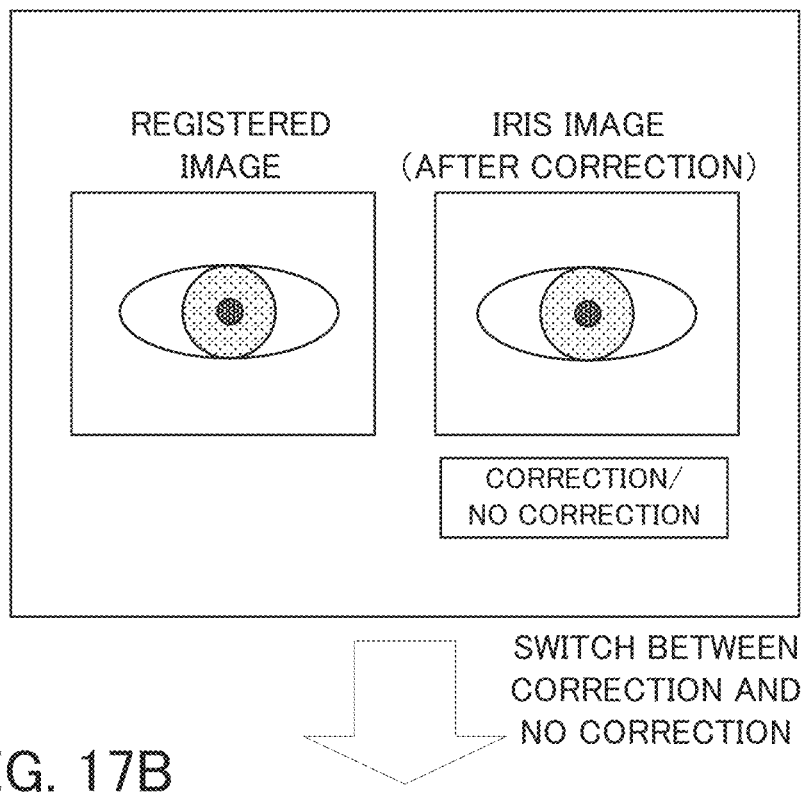
FIG. 17A and FIG. 17B are Version 2 of a diagram illustrating a display example in the imaging system according to the fifth example embodiment.
Figure 17B:
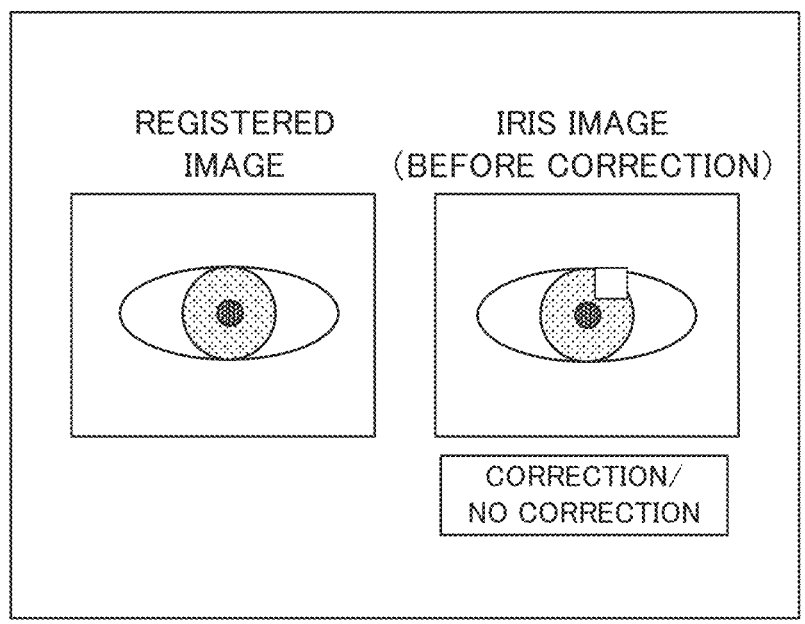

With reference to FIG. 17A and FIG. 17B, a second display example will be described. FIG. 17A and FIG. 17B are Version 2 of a diagram illustrating the display example in the imaging system according to the fifth example embodiment.

As illustrated in FIG. 17A, the display unit 140 may perform display in such a manner that correction/no correction of the iris image is switchable. Specifically, a button for switching between correction and no correction may be displayed below the iris image. In this case, when a button for no correction is pressed, the iris image is displayed in a state before correction (i.e., a state of the imaging in which the correction is not performed by the correction unit 132), as illustrated in FIG. 17B. In this way, it is possible to know what part of the iris image is corrected and how it is corrected. The iris image before correction and the iris image after correction may be displayed simultaneously.

Third Display Example

Figure 18A:
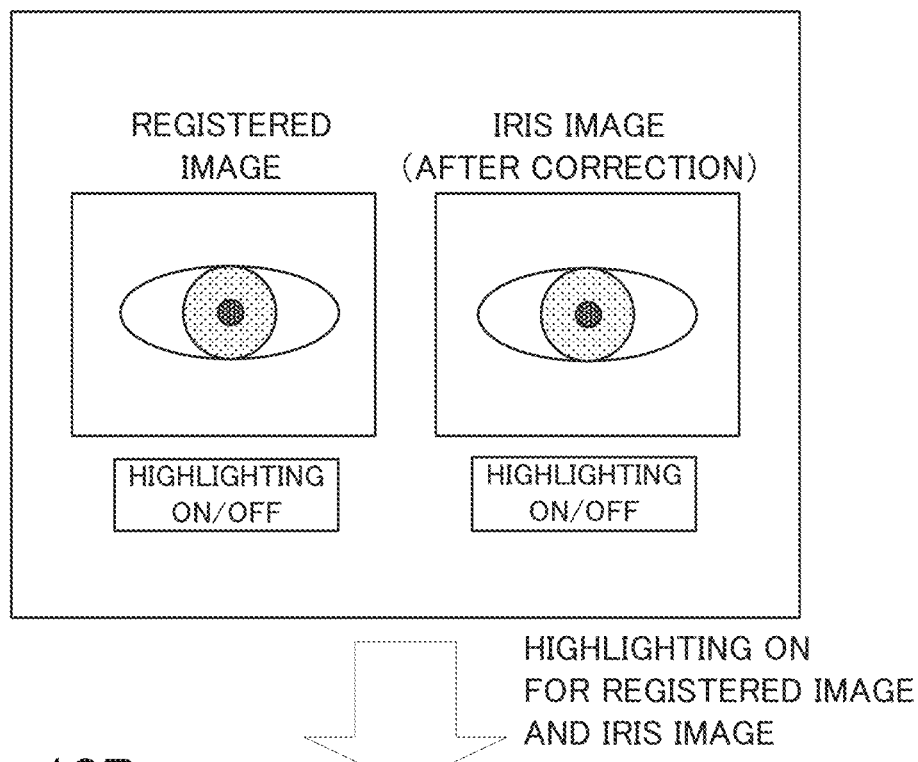
FIG. 18A and FIG. 18B are Version 3 of a diagram illustrating a display example in the imaging system according to the fifth example embodiment.
Figure 18B:
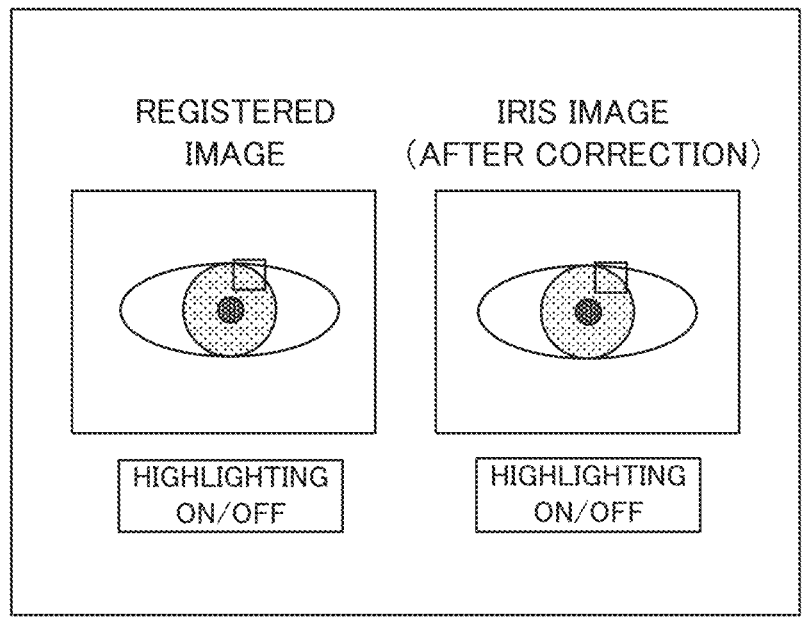

With reference to FIG. 18A and FIG. 18B, a third display example will be described. FIG. 18A and FIG. 18B are Version 3 of a diagram illustrating the display example in the imaging system according to the fifth example embodiment.

As illustrated in FIG. 18A, the display unit 140 may perform display in such a manner that highlighting ON/OFF of a corrected part (in other words, a part corresponding to the second area) is switchable. Specifically, a button for switching between highlighting ON and highlighting OFF may be displayed below the registered image and the iris image. In this case, when the button is pressed such that the highlighting is ON for both the registered image and the iris image, the part corresponding to the second area of each of the registered image and the iris image is surrounded by a frame and displayed, as illustrated in FIG. 18B. In this way, it is possible to know which part of the iris image is corrected. The display of surrounding the part by the frame is an example of the highlighting, and the highlighting may be performed in another aspect (e.g., changing color and density, or flashing, etc.).

Sixth Example Embodiment

The imaging system 10 according to a sixth example embodiment will be described with reference to FIG. 19 and FIG. 20. The sixth example embodiment is partially different from the first to fifth example embodiments described above only in configuration and operation, and may be the same as the first example embodiment, for example, in hardware configuration (see FIG. 1). Therefore, in the following, a description of the parts that overlap those already described will be omitted as appropriate.

Figure 19:
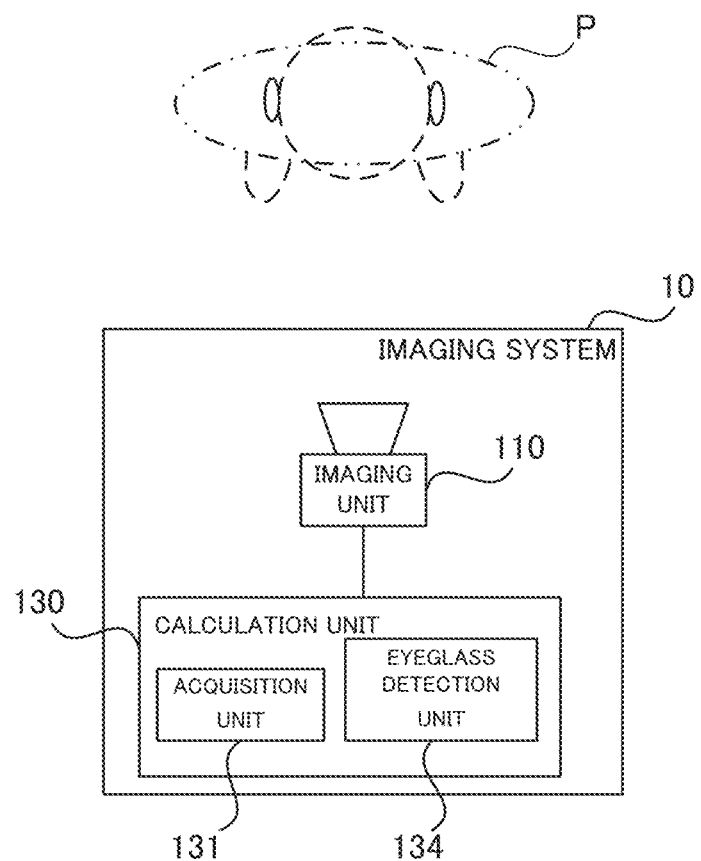
FIG. 19 is a block diagram illustrating a functional configuration of an imaging system according to a sixth example embodiment.

As illustrated in FIG. 19, the imaging system 10 according to the sixth example embodiment includes the imaging unit 110, and the calculation unit 130. In particular, the calculation unit 130 according to the sixth example embodiment includes the acquisition unit 131 and an eyeglass detection unit 134. That is, the calculation unit 130 according to the sixth example embodiment includes the eyeglass detection unit 134 in place of the correction unit 132 in each of the example embodiments described above.

The eyeglass detection unit 134 is configured to detect that the target person P is wearing eyeglasses on the basis of the first information and the second information obtained by the acquisition unit 131. For example, when both the first information and the second information are obtained by the acquisition unit 131, the eyeglass detection unit 134 detects that the target person P is wearing eyeglasses. On the other hand, when only the first information is obtained by the acquisition unit 131, the eyeglass detection unit 134 does not detect the target person P is wearing eyeglasses.

Flow of Operation

Next, with reference to FIG. 20, a flow of operation of the imaging system 10 according to the sixth example embodiment will be described. FIG. 20 is a flowchart illustrating the flow of the operation of the imaging system according to the sixth example embodiment.

As illustrated in FIG. 8, in operation of the imaging system 10 according to the sixth example embodiment, first, the imaging unit 110 captures the image of the eye area of the target person P (step S501). Then, the acquisition unit 131 obtains the first information and the second information (step S502).

Subsequently, the eyeglass detection unit 134 performs an eyeglass detection process on the basis of an acquisition result of the acquisition unit 131 (i.e., the first information and the second information) (step S503). When detecting that the target person P is wearing eyeglasses, the eyeglass detection unit 134 may output the information to the display or the like.

Technical Effect

Next, a technical effect obtained by the imaging system 10 according to the sixth example embodiment will be described.

Figure 20:
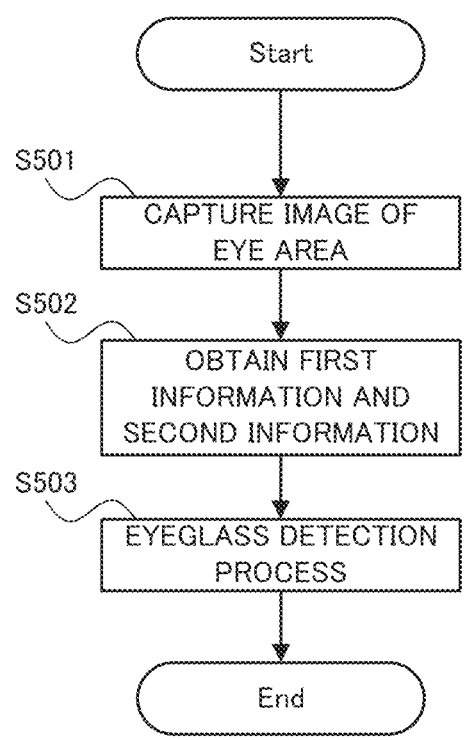
FIG. 20 is a flowchart illustrating a flow of operation of the imaging system according to the sixth example embodiment.

As described in FIG. 19 and FIG. 20, in the imaging system 10 according to the sixth example embodiment, it is detected that the target person P is wearing eyeglasses on the basis of the acquisition result of the acquisition unit 131 (specifically, the first information that does not indicate the reflection of light by the eyeglasses, and the second information that indicates the reflection of light by the eyeglasses). Therefore, it is possible to properly determine whether or not the target person P is wearing eyeglasses, from the image obtained by imaging the target person P.

Supplementary Notes

The example embodiments described above may be further described as, but not limited to, the following Supplementary Notes.

Supplementary Note 1

An imaging system described in Supplementary Note 1 is an imaging system including: an imaging unit that captures an image of an eye area of a target person by using an image sensor that allows imaging without saturating observed light; an acquisition unit that obtains, from the image, a first information about a first area that does not include reflection of light by an eyeglass lens of the target person, and a second information about a second area that includes the reflection of the light; and a correction unit that corrects the second information so as to reduce an influence of the reflection, on the basis of the first information.

Supplementary Note 2

An imaging system described in Supplementary Note 2 is the imaging system described in Supplementary Note 1, further including an irradiation unit that applies illumination light to the eye area.

Supplementary Note 3

An imaging system described in Supplementary Note 3 is the imaging system described in Supplementary Note 1 or 2, further including a generation unit that generates an iris image including iris features of the target person from the first information and from the corrected second information.

Supplementary Note 4

An imaging system described in Supplementary Note 4 is the imaging system described in any one of Supplementary Notes 1 to 3, wherein, the imaging unit captures a plurality of images in two or more different brightness ranges, and the acquisition unit obtains each of the first information and the second information from the images captured in different brightness ranges.

Supplementary Note 5

An imaging system described in Supplementary Note 5 is the imaging system described in Supplementary Note 4, wherein the acquisition unit selects a non-saturated image in which a pixel value of the second area is not saturated from the images captured in different brightness ranges, and obtains the second information from the non-saturated image.

Supplementary Note 6

An imaging system described in Supplementary Note 6 is the imaging system described in any one of Supplementary Notes 1 to 5, wherein the correction unit corrects the second information by subtracting a value based on an average value of pixel values of the first area from an average value of pixel values of the second area.

Supplementary Note 7

An imaging system described in Supplementary Note 7 is the imaging system described in any one of Supplementary Notes 1 to 6, further including a display unit that displays at least one of an iris image and a registered image used for an authentication process of the iris image.

Supplementary Note 8

An imaging system described in Supplementary Note 8 is the imaging system described in Supplementary Note 7, wherein the display unit displays the iris image and the image captured by the imaging unit, simultaneously or alternatively.

Supplementary Note 9

An imaging system described in Supplementary Note 9 is the imaging system described in Supplementary Note 7 or 8, wherein the display unit highlights at least one of a part corresponding to the second area of the iris image and a part corresponding to the second area of the registered image.

Supplementary Note 10

An imaging system described in Supplementary Note 10 is the imaging system described in Supplementary Note 9, wherein the display unit is configured to switch between presence and absence of highlighting.

Supplementary Note 11

An imaging method described in Supplementary Note 11 is an imaging method including: capturing an image of an eye area of a target person by using an image sensor that allows imaging without saturating observed light; obtaining, from the image, a first information about a first area that does not include reflection of light by an eyeglass lens of the target person, and a second information about a second area that includes the reflection of the light; and correcting the second information so as to reduce an influence of the reflection, on the basis of the first information.

Supplementary Note 12

A computer program described in Supplementary Note 12 is a computer program that operates a computer: to capture an image of an eye area of a target person by using an image sensor that allows imaging without saturating observed light; to obtain, from the image, a first information about a first area that does not include reflection of light by an eyeglass lens of the target person, and a second information about a second area that includes the reflection of the light; and to correct the second information so as to reduce an influence of the reflection, on the basis of the first information.

Supplementary Note 13

An imaging system described in Supplementary Note 13 is an imaging system including: an imaging unit that captures an image of an eye area of a target person by using an image sensor that allows imaging without saturating observed light; an acquisition unit that obtains, from the image, a first information about a first area that does not include reflection of light by an eyeglass lens of the target person, and a second information about a second area that includes the reflection of the light; and a detection unit that detects eyeglasses of the target person on the basis of an acquisition result of the acquisition unit.

Supplementary Note 14

An imaging method described in Supplementary Note 14 is an imaging method including: capturing an image of an eye area of a target person by using an image sensor that allows imaging without saturating observed light; obtaining, from the image, a first information about a first area that does not include reflection of light by an eyeglass lens of the target person, and a second information about a second area that includes the reflection of the light; and detecting eyeglasses of the target person on the basis of an acquisition result of the acquisition unit.

Supplementary Note 15

A computer program described in Supplementary Note 15 is a computer program that operates a computer: to capture an image of an eye area of a target person by using an image sensor that allows imaging without saturating observed light; to obtain, from the image, a first information about a first area that does not include reflection of light by an eyeglass lens of the target person, and a second information about a second area that includes the reflection of the light; and to detect eyeglasses of the target person on the basis of an acquisition result of the acquisition unit.

Supplementary Note 16

A recording medium described in Supplementary Note 16 is a recording medium on which the computer program described in Supplementary Note 12 or 15 is recorded.

This disclosure is not limited to the examples described above and is allowed to be changed, if desired, without departing from the essence or spirit of the invention which can be read from the claims and the entire specification. An imaging system, an imaging method, and a computer program with such modifications are also intended to be within the technical scope of this disclosure.

DESCRIPTION OF REFERENCE CODES

10 Imaging system
11 Processor
110 Imaging unit
111 Lens
112 Image sensor
120 Irradiated unit
130 Calculation unit
131 Acquisition unit
132 Correction unit
133 Generation unit
134 Eyeglass detection unit
140 Display unit
200 Eyeglass lens
P Target person

What is claimed is:

1. An imaging system comprising:
   a camera that captures an image of an eye area of a target person by using an image sensor that allows imaging without saturating observed light;
   at least one memory storing instructions; and
   at least one first processor that is configured to execute the instructions to
   obtain, from the image, a first information about a first area that does not include reflection of light by an eyeglass lens of the target person, and a second information about a second area that includes the reflection of the light; and
   correct the second information so as to reduce an influence of the reflection, on the basis of the first information by subtracting a value based on an average value of pixel values of the first area from an average value of pixel values of the second area.

2. The imaging system according to claim 1, further comprising a second processor that is configured to execute instructions to apply illumination light to the eye area.

3. The imaging system according to claim 1, further comprising a third processor that is configured to execute instructions to generate an iris image including iris features of the target person from the first information and from the corrected second information.

4. The imaging system according to claim 1, wherein
   the camera captures a plurality of images in two or more different brightness ranges, and
   the at least one first processor is configured to execute the instructions to obtain each of the first information and the second information from the images captured in different brightness ranges.

5. The imaging system according to claim 4, wherein the at least one first processor is configured to execute the instructions to select a non-saturated image in which a pixel value of the second area is not saturated from the images captured in different brightness ranges, and obtain the second information from the non-saturated image.

6. The imaging system according to claim 1, further comprising a display that displays at least one of an iris image and a registered image used for an authentication process of the iris image.

7. The imaging system according to claim 6, wherein the display displays the iris image and the image captured by the camera, simultaneously or alternatively.

8. The imaging system according to claim 6, wherein the display highlights at least one of a part corresponding to the second area of the iris image and a part corresponding to the second area of the registered image.

9. The imaging system according to claim 8, wherein the display is configured to switch between presence and absence of highlighting.

10. An imaging method comprising:
    capturing an image of an eye area of a target person by using an image sensor that allows imaging without saturating observed light;
    obtaining, from the image, a first information about a first area that does not include reflection of light by an eyeglass lens of the target person, and a second information about a second area that includes the reflection of the light; and
    correcting the second information so as to reduce an influence of the reflection, on the basis of the first information by subtracting a value based on an average value of pixel values of the first area from an average value of pixel values of the second area.

11. A non-transitory recording medium storing a computer program executable by a computer to perform an imaging method comprising:
    capturing an image of an eye area of a target person by using an image sensor that allows imaging without saturating observed light;
    obtaining, from the image, a first information about a first area that does not include reflection of light by an eyeglass lens of the target person, and a second information about a second area that includes the reflection of the light; and
    correcting the second information so as to reduce an influence of the reflection, on the basis of the first information by subtracting a value based on an average value of pixel values of the first area from an average value of pixel values of the second area.

* * * * *